(12) United States Patent
Hoernig

(10) Patent No.: US 8,804,903 B2
(45) Date of Patent: Aug. 12, 2014

(54) MAMMOGRAPHY APPARATUS

(75) Inventor: Mathias Hoernig, Erlangen (DE)

(73) Assignee: Siemens Aktiengesellschaft, Munich (DE)

( * ) Notice: Subject to any disclaimer, the term of this patent is extended or adjusted under 35 U.S.C. 154(b) by 304 days.

(21) Appl. No.: 13/234,408

(22) Filed: Sep. 16, 2011

(65) Prior Publication Data

US 2012/0069959 A1  Mar. 22, 2012

(30) Foreign Application Priority Data

Sep. 22, 2010 (DE) .......................... 10 2010 041 205

(51) Int. Cl.
*A61B 6/04* (2006.01)

(52) U.S. Cl.
USPC .......................................... 378/37; 378/208

(58) Field of Classification Search
USPC .......................................... 378/37, 208–209
See application file for complete search history.

(56) References Cited

U.S. PATENT DOCUMENTS

| 5,609,152 | A | * | 3/1997 | Pellegrino et al. | 378/37 |
| 6,038,718 | A | * | 3/2000 | Pennington et al. | 5/618 |
| 6,128,523 | A |   | 10/2000 | Bechtold et al. | |
| 2008/0043905 | A1 | * | 2/2008 | Hassanpourgol | 378/37 |

FOREIGN PATENT DOCUMENTS

WO          00/16695        9/1999

* cited by examiner

*Primary Examiner* — Hoon Song
(74) *Attorney, Agent, or Firm* — Schiff Hardin LLP

(57) ABSTRACT

A mammography apparatus has a bed unit on which, during a screening, the patient lies ventrally on a recumbent surface of the bed unit. The recumbent surface has a configuration allowing variable individual parts of the bed unit to be positioned so that the bed position of the patient is optimized and the components of the x-ray unit that are arranged below the bed unit can be positioned and aligned relative to one another such that the base of the breast to be x-rayed is also imaged.

20 Claims, 2 Drawing Sheets

MAMMOGRAPHY APPARATUS

BACKGROUND OF THE INVENTION

1. Field of the Invention

The invention concerns a mammography apparatus, in particular a mammography apparatus in which the patient is positioned ventrally on a recumbent surface of a bed unit during the x-ray acquisitions.

2. Description of the Prior Art

In order to create an x-ray exposure of the breast of the patient in the recumbent position, the bed unit has an opening at the level of the breast. Individual exposures of the breast of the patient are created for diagnosis, or a number of x-ray exposures from different angle positions are created to calculate slice images. For this purpose, an x-ray head is directed on an orbit around the breast to be examined, for example.

SUMMARY OF THE INVENTION

An object of the invention is to provide an additional embodiment of a bed unit with an x-ray mammography system.

The object is achieved in accordance with the invention by a mammography apparatus having an x-ray unit, formed by an x-ray source and a detector, located below a recess of the bed (the recess being located in the breast region of a ventrally positioned patient). The bed unit is subdivided into at least a first part and second bed part and the bed parts can be aligned relative to one another to cause the x-ray source and the detector to be positioned at the underside of the bed unit so that the entire breast (chest wall region)—with the base of the breast being irradiated by x-rays and imaged in an x-ray image detected by the detector.

The invention has the advantage that x-ray acquisition cycles can be implemented with different diagnostic focal points of the breast. Acquisition scenarios—for example for a spiral CT, a cone beam CT, a FFDM CT with biopsy or therapy functionality—can be implemented with one and the same mammography device.

The invention has the advantage that the entire breast can be irradiated and imaged in x-ray exposures for different examination methods. The invention has the advantage that the base of the breast is acquired in an x-ray scan in order to image the entire breast in 2D or 3D x-ray image.

The invention also has the advantage that the patient occupies an ergonomic recumbent position during the x-ray acquisitions.

The invention has the further advantage that the x-ray unit can be used flexibly because the recumbent surface of the bed unit can be of varied by selective positioning of the bed parts.

The invention also has the advantage that, by tilting the x-ray source/detector combination during a scan, it is prevented that structures along the primary beam direction are distributed among multiple slices given a tomosynthesis.

The invention also has the advantage that the position of the bed unit and the settings of the x-ray unit can be stored relative to the patient, and can already be set for that patient at the beginning of the screenings in subsequent acquisition sessions.

DESCRIPTION OF THE PREFERRED EMBODIMENTS

In the mammography apparatus shown in the figures, the patient lies ventrally on a recumbent surface of a bed unit that can be of variable design, wherein individual portions of the recumbent surface of the bed unit can be positioned so that on the one hand the bed position of the patient is optimized and on the other hand the components of the x-ray unit that are arranged below the bed unit can be positioned and aligned relative to one another such that the base of the breast of a breast to be x-rayed is also imaged in x-ray exposures.

Figure 1:
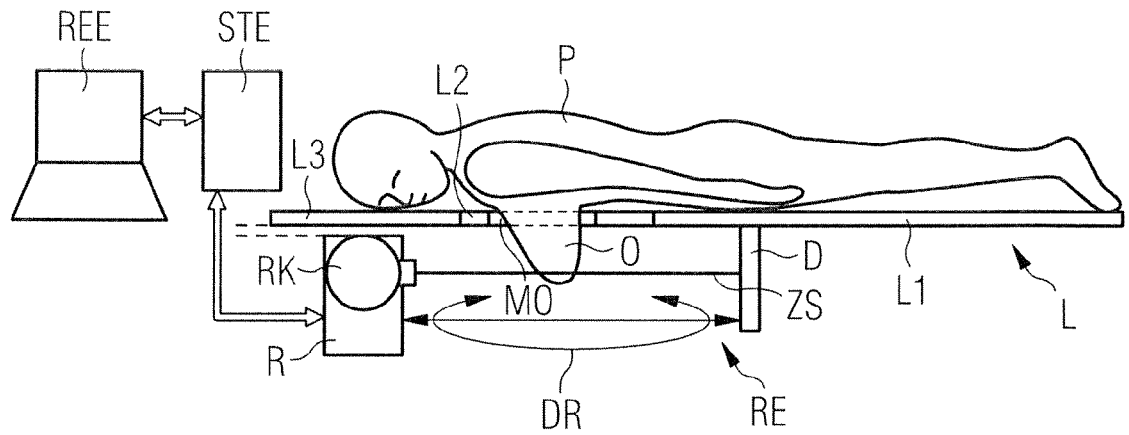
FIG. 1 is a mammography apparatus with bed unit.

A mammography apparatus with a bed unit L and an x-ray unit RE (formed by an x-ray radiator R having at least one x-ray source RK and a detector D) for the examination of the breast O of a patient P are schematically indicated in FIG. 1. A control unit STE and an associated computer REE are schematically indicated. In the computer REE the x-ray images of an acquisition cycle are converted into a volume image. The bed unit L is also designated as a prone table. The image shows a side view of the bed unit L. In the region of the upper body of the patient the bed unit L has at least one opening MO. The x-ray source RK and the detector unit D are arranged directly below the opening MO of the recumbent surface of the bed unit L. This x-ray unit RE is designed such that both the detector D and the x-ray source RK can be respectively be adjusted in terms of height and can be tilted and aligned relative to one another (see FIGS. 3 and 4). The x-ray device R has at least one x-ray source RK arranged below the recumbent surface of the bed unit L on the facing side or at the head end of the bed unit L. Relative to the x-ray source RK the detector unit D—a flat panel detector—on the underside of the bed unit L is aligned towards the x-ray source RK. The controllable mechanism accommodating the x-ray source RK and the detector D is fashioned so that the x-ray source and the detector can be rotated around the breast, matching one another. The x-ray unit is additionally fashioned so that it can be moved in terms of its height. In order to allow the x-rays emitted by the x-ray source RK to strike closer to the base of the breast, a portion of the bed unit L is designed such that—in addition to a partially height-adjustable head region—the bed unit L has depressions on its underside in the head region (see FIG. 4). The depressions are semicircular in design below the head region of the bed unit L. This embodiment has the advantage that the base of the breast can be acquired with the x-rays emitted by the x-ray source and can be imaged at the detector. Among other things, the bed unit L is comprised of x-ray-impermeable materials. The shown rotation direction DR of the x-ray device RE indicates that this can be controlled so as to be able to rotate both clockwise and counter-clockwise around the subject O to be examined.

Figure 2:
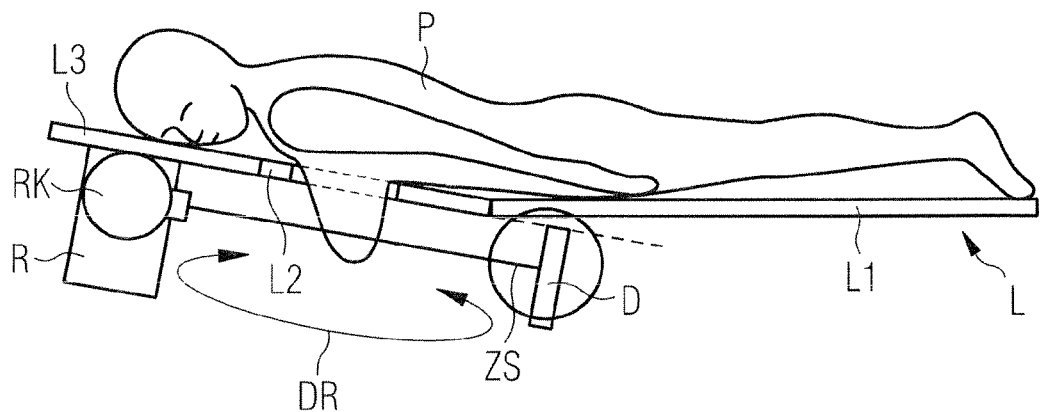
FIG. 2 shows an embodiment of the invention.

An embodiment variant of the bed unit L with the associated x-ray unit RE is indicated in FIG. 2. In this embodiment variant the bed unit L has a first bed part L1 and a second bed part L2. As shown the bed unit L subdivided—approximately in the area of its middle into a first bed part L1 and a second bed part L2. The second bed part L2 can be tilted or engaged by an angle in an angle range between 0 and 30° relative to the patient. Instead of the second bed part L2, the first bed part can also be engaged in a predeterminable angle range so that the upper body of the patient lies horizontally and the pelvis and the legs of the patient lie on the angled first bed part. In a further embodiment both bed parts can be angled relative to one another. The x-ray device R—in particular the x-ray source RK—is arranged directly below the underside of the second bed part L2. While the detector D in FIG. 1 is still aligned orthogonally to the underside of the bed L, in the embodiment according to FIG. 2 the detector is aligned such that this is arranged displaced from the underside of the first bed part L1. The detector D is aligned on the x-ray source RK such that, given an imaginary extension of the second bed part L2, said detector can be aligned perpendicular to the imaginary extension. For example, the components of the x-ray unit RE can be positioned below the bed unit L via singly or multiply articulated robot arms. A central ray ZS of the x-ray source RK is depicted as an example in FIG. 2.

Figure 3:
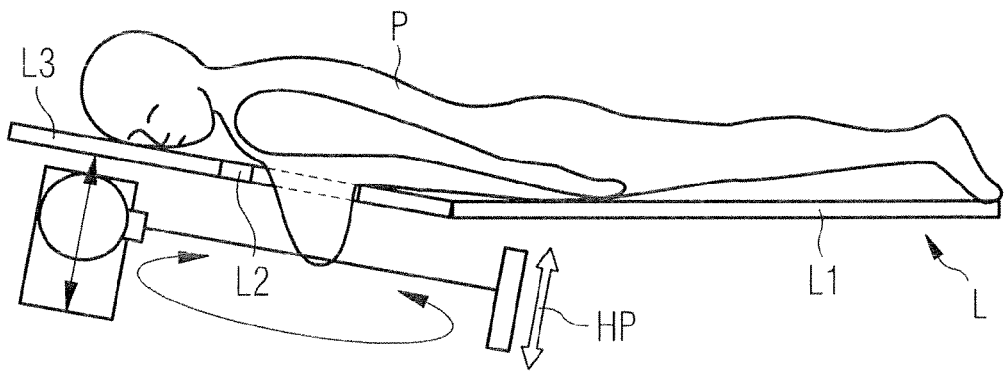
FIG. 3 is an additional embodiment of the invention.

In FIG. 3 the bed unit L shown in FIG. 2 is modified such that the distance between x-ray unit RE and the underside of the bed unit L is variable. The spacing of the x-ray unit RE from the underside of the bed unit L can be varied during a screening. Here the spacing can also be produced by raising the bed unit L.

Figure 4:
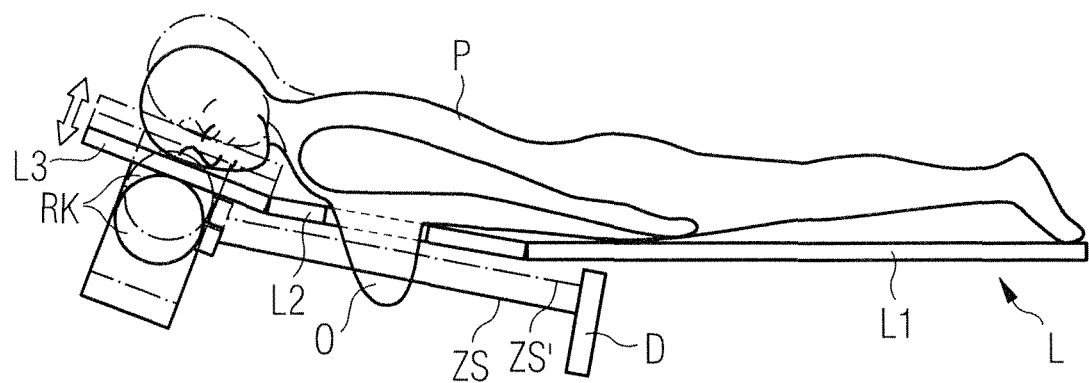
FIG. 4 shows another embodiment of the invention.

An additional embodiment variant of the bed unit L shown in FIGS. 2, 3 is shown with associated x-ray unit RE in FIG. 4. This bed unit is subdivided into a first bed part L1, a second bed part L2 and a third bed part L3. In contrast to the bed unit L shown in FIGS. 2 and 3, the recumbent surface of the second bed part L2 has an additional subdivision. In this embodiment variant the third bed part L3 is arranged in the region of the head of the patient. Via this bed device an increased comfort is offered to the patient with regard to the bed position. The present embodiment has the additional advantage that the x-ray source RK emits the x-rays in a direction so that the base of the breast of the patient is irradiated and detected by the subsequent detector D. The third bed part L3 can be arranged variably at the second bed part L2 in such a manner that either an additional angle can be generated in the recumbent surface of the bed unit L, or that the third bed part L3 can be arranged such that it can be offset corresponding to the direction indicated in FIG. 4. The length of the third bed part L3 depends on the capability to position the head of the patient P and on the measurements of the x-ray head RK and a possible trajectory of the x-ray head RK in a screening. The underside of the bed unit L can be modified with regard to the positioning capability of the x-ray head RK to the effect that depressions are introduced into the underside of the bed unit L (for example in the head and upper body region). In one embodiment variant it is likewise possible that the surface of the first and second bed part L1, L2 lies in one plane and the third bed part L3 is arranged offset in terms of its height corresponding to the arrow direction indicated in FIG. 4. This embodiment is to be applied when a trajectory of the x-ray head does not require 360°. In the variant shown in FIG. 4 the central ray ZS, ZS' can approach the base of the breast. The bed unit of the mammography apparatus can also be developed such that this is adjustable in its height while the components of the x-ray unit are directed on a trajectory around the breast. The recumbent surface of the bed unit L has at least one x-ray-impermeable slice. All alignments of the bed parts L1, L2, L3, . . . of the bed unit are adjustable either manually or by means of electric motors.

Figure 5:
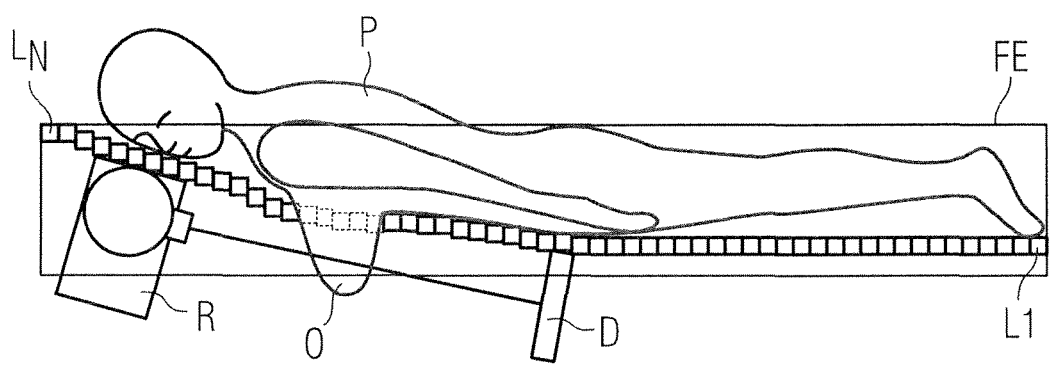
FIG. 5 shows another embodiment of the invention.

An additional embodiment of a recumbent surface of the bed unit L is depicted in FIG. 5. In this embodiment the recumbent surface is subdivided into a plurality of bed parts L1, . . . , Ln. The individual bed parts L1, . . . , Ln are height-adjustable. Guide elements FE are arranged on both sides of the bed parts. Guide rails are integrated into the guide elements FE. Here multiple bed parts L1+x, . . . , Ln−y can respectively be assembled so as to be height-adjustable in a guide rail. The structure can also be designed so that each bed part is height-adjustable. The bed parts L1, . . . , Ln can likewise be moved by means of motors in the guide rails. The advantage of the lateral height adjustment of the bed parts exists in the space savings below the recumbent surface. This freed space can be used for the x-ray radiator-detector unit RE. In addition, the guide elements arranged on both sides form a fixing capability for the patient.

Although modifications and changes may be suggested by those skilled in the art, it is the intention of the inventor to embody within the patent warranted hereon all changes and modifications as reasonably and properly come within the scope of his contribution to the art.

I claim as my invention:

1. A mammography apparatus comprising:
    a bed unit having a bed unit surface configured to receive a ventrally positioned female patient thereon, said bed unit surface having a recess therein at a location allowing a breast of the ventrally positioned patient to proceed through said recess;
    an x-ray unit comprising an x-ray source and a radiation detector, said x-ray unit being located beneath said bed unit surface of said bed unit;
    said bed unit being subdivided into a plurality of bed parts, including at least a first bed part and second bed part, that are selectively moveable with respect to each other to form said bed unit into a configuration, dependent on individual anatomy and size of the female patient, that allows positioning of said x-ray source and said radiation detector beneath said bed unit surface to cause an entirety of the breast proceeding through the recess to be irradiated by x-rays from said x-ray source and imaged in an x-ray image detected by said radiation detector; and
    at least one of said bed parts being moveable to produce a depression in an underside of said bed unit, opposite to said bed unit surface, configured to permit said x-ray source to be received in said depression to cause said x-ray source to irradiate a base of the breast in the recess and to permit said radiation detector to detect x-rays irradiated by the x-ray source and attenuated by the base of the breast proceeding through the recess, while said radiation detector remains stationary.

2. A mammography apparatus as claimed in claim 1 wherein individual bed parts in said plurality of bed parts are selectively tiltable relative to one another.

3. A mammography apparatus as claimed in claim 1 wherein at least one of said bed parts is height adjustable, said at least one of said parts that is height-adjustable being located in a head region of the ventrally positioned patient.

4. A mammography apparatus as claimed in claim 1 wherein each bed part in said plurality of bed parts is height-adjustable.

5. A mammography apparatus as claimed in claim 1 wherein said x-ray unit is mounted beneath said bed unit surface with a variable spacing between said x-ray unit and said bed unit surface.

6. A mammography apparatus as claimed in claim 1 wherein said x-ray source is displaceable within said x-ray device.

7. A mammography apparatus as claimed in claim 1 wherein said x-ray source emits said x-rays in a radiation propagation direction that is variable.

8. A mammography apparatus as claimed in claim 1 wherein said radiation detector is mounted within said x-ray device so as to track said propagation direction as said propagation direction is varied.

9. A mammography apparatus as claimed in claim 1 wherein said x-ray unit is located beneath said bed unit surface so as to be rotatable around the breast proceeding through the recess.

10. A mammography apparatus as claimed in claim 1 wherein said bed unit parts are height adjustable simultaneously with rotation of said x-ray unit in a trajectory around the breast proceeding through the recess.

11. A mammography apparatus comprising:
- a bed unit having a bed unit surface configured to receive a ventrally positioned female patient thereon, said bed unit surface having a recess therein at a location allowing a breast of the ventrally positioned patient to proceed through said recess;
- an x-ray unit comprising an x-ray source and a radiation detector, said x-ray unit being located beneath said bed unit surface of said bed unit;
- said bed unit being subdivided into a plurality of bed parts, including at least a first bed part and second bed part, that are selectively moveable with respect to each other to form said bed unit into a configuration, dependent on individual anatomy and size of the female patient, that allows positioning of said x-ray source and said radiation detector beneath said bed unit surface to cause an entirety of the breast proceeding through the recess to be irradiated by x-rays from said x-ray source and imaged in an x-ray image detected by said radiation detector; and
- at least one of said bed parts being moveable to produce a depression in an underside of said bed unit, opposite to said bed unit surface, configured to permit said x-ray source to be received in said depression to cause said x-ray source to irradiate a base of the breast in the recess and to permit said radiation detector to detect x-rays irradiated by the x-ray source and attenuated by the base of the breast proceeding through the recess, while the x-ray source and the radiation detector move in a trajectory around the base of the breast proceeding through the recess.

12. A mammography apparatus as claimed in claim 11 wherein individual bed parts in said plurality of bed parts are selectively tiltable relative to one another.

13. A mammography apparatus as claimed in claim 11 wherein at least one of said bed parts is height adjustable, said at least one of said parts that is height-adjustable being located in a head region of the ventrally positioned patient.

14. A mammography apparatus as claimed in claim 11 wherein each bed part in said plurality of bed parts is height-adjustable.

15. A mammography apparatus as claimed in claim 11 wherein said x-ray unit is mounted beneath said bed unit surface with a variable spacing between said x-ray unit and said bed unit surface.

16. A mammography apparatus as claimed in claim 11 wherein said x-ray source is displaceable within said x-ray device.

17. A mammography apparatus as claimed in claim 11 wherein said x-ray source emits said x-rays in a radiation propagation direction that is variable.

18. A mammography apparatus as claimed in claim 11 wherein said radiation detector is mounted within said x-ray device so as to track said propagation direction as said propagation direction is varied.

19. A mammography apparatus as claimed in claim 11 wherein said x-ray unit is located beneath said bed unit surface so as to be rotatable around the breast proceeding through the recess.

20. A mammography apparatus as claimed in claim 11 wherein said bed unit parts are height adjustable simultaneously with rotation of said x-ray unit in a trajectory around the breast proceeding through the recess.

* * * * *